Figure 1:
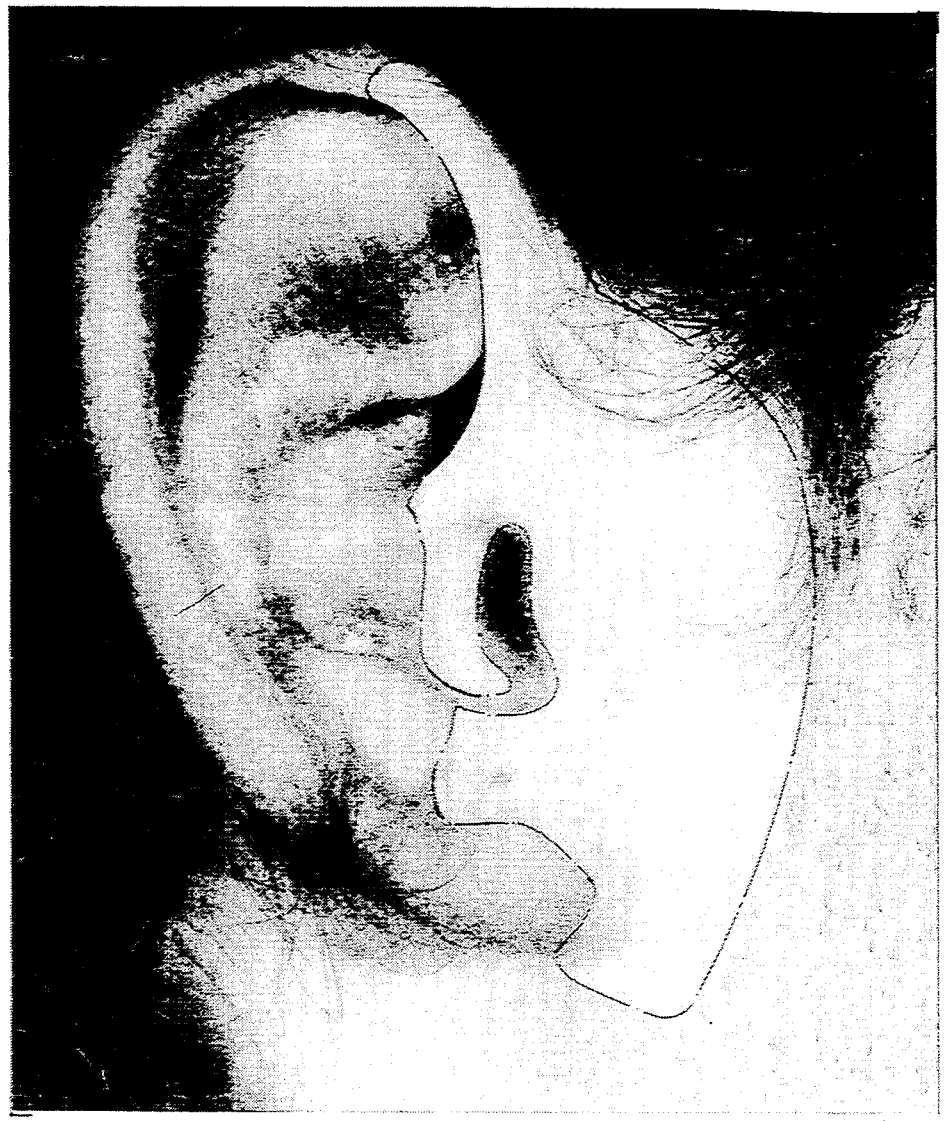
Figure 2:

United States Patent [19]

Wood et al.

[11] Patent Number: 5,433,942
[45] Date of Patent: Jul. 18, 1995

[54] COMPOSITION AND METHOD OF TREATING DEPIGMENTATION DISORDERS

[75] Inventors: John M. Wood; Karin U. Schallreuter, both of Quickborn, Germany

[73] Assignee: Stiefel Laboratories, Inc., Coral Gables, Fla.

[21] Appl. No.: 150,014

[22] PCT Filed: May 15, 1992

[86] PCT No.: PCT/GB92/00878

§ 371 Date: Nov. 15, 1993

§ 102(e) Date: Nov. 15, 1993

[87] PCT Pub. No.: WO92/20354

PCT Pub. Date: Nov. 26, 1992

[30] Foreign Application Priority Data

May 15, 1991 [GB] United Kingdom ............... 9110652

[51] Int. Cl.⁶ ................. A61K 38/44; A61K 33/34; A61K 33/32; A61K 7/42
[52] U.S. Cl. ..................................... 424/59; 424/63; 424/639; 424/630; 424/648; 424/944
[58] Field of Search ............... 424/63, 639, 630, 648, 424/94.4, 59

[56] References Cited

U.S. PATENT DOCUMENTS 4,129,644 12/1978 Kalopissis et al. ................. 424/59

FOREIGN PATENT DOCUMENTS

| | | |
|---|---|---|
| 518946 | 8/1980 | Australia . |
| 544544 | 2/1982 | Australia . |
| 0424033A2 | 4/1991 | European Pat. Off. . |
| 196107A | 4/1989 | Japan . |
| 2108612A | 4/1990 | Japan . |
| 128311 | 7/1965 | New Zealand . |
| 144208 | 10/1968 | New Zealand . |
| 188912 | 5/1984 | New Zealand . |
| 198416 | 7/1984 | New Zealand . |

OTHER PUBLICATIONS

Kono et al., J. Biol. Chem. 258(10): 6015–6019 (1983).
Kono et al., Chemical Abstracts, 114(21):202133d, 2(1), pp. 18–26 (1990).

Primary Examiner—Marion C. Knode
Assistant Examiner—Jean C. Witz
Attorney, Agent, or Firm—Mathews, Woodbridge & Collins

[57] ABSTRACT

Vitiligo and other tyrosinase-positive depigmentation disorders are treated by topical application of a pseudocatalase and subsequent exposure to a sub-minimal erythema dose of UVB light. After a course of treatment, pigmentation of the affected areas can be maintained by treatment with the pseudocatalases without UVB light treatment. The preferred pseudocatalases are transition metal co-ordination complexes, especially manganese (II) bicarbonate.

16 Claims, 2 Drawing Sheets

(BEFORE TREATMENT)

(AFTER TREATMENT)

COMPOSITION AND METHOD OF TREATING DEPIGMENTATION DISORDERS

This application was filed under 35 USC § 371 through PCT/GB92/00878, filed May 15, 1992.

The present invention relates to the treatment of tyrosinase-positive depigmentation disorders and has particular application to the treatment of vitiligo. It provides compositions for said treatment and methods of said treatment.

Vitiligo is a chronic depigmentation disorder in which the patient has unsightly white patches or spots which are caused by localized loss of pigment and are very liable to sunburn. Although the condition is not debilitating, it is often emotionally stressful to the patient. The cause presently is unknown but it has been speculated that it results from an autoimmune response, involvement of the nervous system or a toxic effect on melanocytes. Usually, the only treatment is the use of skin-colouring cosmetics to disguise the patches or, in the case of Blacks and Indians, of depigmenting agents such as hydroquinone to depigment the remaining pigmented skin. Some limited success in treatment has been reported using the so-called PUVA method.

In the PUVA method, methoxsalen (ie. 8-methoxy psoralen) or, less usually, other psoralens is administered orally and the patient subsequently exposed to UVA light. Psoralens are plant extracts and have been known since ancient Egyptian times to act as photosensitizers. The psoralen is given systemically and hence the photosensitizing effect is not localized and, since this effect is in the UVA range (320–400 nm), the patient must wear special glasses during everyday life in order to prevent eye damage. Further, side effects of PUVA include nausea, erythema, oedema, dizziness, headache, vesiculation, bulla formation, onycholysis, acneiform eruption and severe skin pain. Long term risks include skin cancer, epidermal dystrophy, premature skin aging, cataract formation, and alterations in the immune system. The treatment is believed to be toxic to normal lymphocytes and Langerhans' cells. Accordingly, the treatment usually is limited to elderly patients or to two years duration. It has recently been proposed to mitigate some of the risks of PUVA by bathing the patient in a psoralen bath.

Other tyrosinase-positive depigmentation disorders include Hermansky-Pudlak Syndrome.

It has now surprisingly been found that vitiligo and other tyrosinase-positive depigmentation disorders can be effectively treated by exposing a patient to UVB light (290–320 nm) after topical application of manganese (II) bicarbonate or other pseudocatalase. Further, it has been found that, following pigmentation by said treatment, a level of pigmentation in affected areas can be retained, at least for a period of time, by topical application of the pseudocatalase without UVB exposure.

We have disclosed in a co-pending Patent Application of the same priority and filing dates and corresponding to UK Patent Application No. 9110651 that pseudocatalase can be used topically to enhance sun tanning.

By pseudocatalase, we mean a plasma membrane permeable physiologically acceptable compound which catalyzes the dismutation of $H_2O_2$ in vivo in analogous manner to catalase.

Without wishing to be bound to any particular hypothesis, it is believed that vitiligo and other tyrosinase-positive depigmentation disorders are caused by a deficiency of catalase which permits a higher than normal peroxide ion concentration in melanocytes. Since tyrosinase is inactivated by peroxide ion, the tyrosinase-catalyzed oxidation of 1-tyrosine to 1-dopa required for melanin biosynthesis is inhibited. Further, since peroxide ion is photochemically reduced to hydroxyl ion, there is a concomitant increase in hydroxyl ion production.

Exposure of the skin to UVB radiation generates superoxide anion radicals which is a preferred substrate for human tyrosinase (40 times better than oxygen) thereby promoting melanin formation. However, the superoxide anion radicals are dismutated into dioxygen and peroxide ion causing an undesirable increase in hydroxyl ion concentration unless catalase or some other competing mechanism removes peroxide ion. Thus, the presence of a pseudocatalase is believed to allow sufficient UVB exposure for superoxide anion radical formation to promote pigmentation in catalase deficient areas without burning or other cell damage.

According to a first aspect of the present invention, there is provided the use of a pseudocatalase in the manufacture of a topical medicament for the treatment of a tyrosinase-positive depigmentation disorder.

In a second aspect, the invention provides a topical composition comprising a pseudocatalase and a physiologically acceptable topical vehicle therefor.

In a third aspect, the invention provides a pseudocatalase for use in the treatment of a tyrosinase-positive depigmentation disorder.

In a fourth aspect, the invention provides a method of treating a tyrosinase-positive depigmentation disorder which comprises applying to at least the depigmented areas of the skin of a patient suffering therefrom an effective amount of a pseudocatalase and thereafter exposing the treated skin to UVB light to induce melanin formation in the depigmented areas.

As mentioned previously, the invention has particular application to the treatment of vitiligo but can be applied to the treatment of other tyrosinase-positive depigmentation disorders, for example Hermansky-Pudlak Syndrome.

The pseudocatalase can be any physiologically acceptable compound which catalyzes the dismutation of hydrogen peroxide. Some compounds such as Mn(II) bicarbonate are already known to be pseudocatalases and others can be determined by simple screening tests.

The presently preferred pseudocatalases are transition metal co-ordination complexes in which the inductive effect of the electron acceptor ligand enhances the redox effect of the metal on hydrogen peroxide dismutation. Usually, the metal will be Cu(I), Fe(II) or, especially Mn(II) and the ligand will be bicarbonate. It is especially preferred that the pseudocatalase is Mn(II) bicarbonate complex. Said complex readily can be prepared by contacting manganous chloride with excess bicarbonate in aqueous solution.

The pseudocatalase is formulated in a topical vehicle for use. Conveniently, the vehicle comprises a hydrophilic cream to which an aqueous solution Or suspension of the pseudocatalase is added to form a cream or lotion. Alternatively, the vehicle can be a bath oil although any other compatible topical vehicle can be used to provide a topical composition.

Preferably, the composition contains calcium ions, suitably added as calcium chloride, to compensate for a calcium defect which appears to be present in vitiliginous skin. Usually, the calcium ion concentration will be 5 to 20 millimolar.

The composition can contain components such as emollients, perfumes etc conventionally used in topical preparations.

Usually, the topical composition is applied twice a day to at least the depigmented areas of skin, usually to the entire skin surface. After at least one of said applications, the patient is exposed to UVB light after a short delay, usually about 20 to 60 minutes, to allow for transport of the pseudocatalase into the epidermis. The UVB exposure is limited to prevent erythema and is increased over the period of treatment from a few seconds to about 5 minutes as the minimal erythema dose increases with UVB tolerance. The course of treatment is continued for several months until there is an acceptable level of pigmentation in the previously depigmented areas. Thereafter, pigmentation is maintained by continuing daily application of the topical composition, possibly with reduced frequency, without UVB exposure. If and when pigment is lost from the affected areas, the exposure to UVB light is recommenced for as long as necessary to restore pigmentation.

The invention is illustrated in the following non-limiting Examples.

EXAMPLE I

Manganous chloride (380 mg) was added to a solution of sodium bicarbonate (2.3 g) in purified water (3.0 ml) at ambient temperature. The mixture was allowed to stand until the evolution of gas had ceased. The resultant pinkish brown liquid was mixed with a hydrophilic cream (100 g, Neribase) to provide a white cream.

Neribase is a cream vehicle containing Macrogol stearate 2000; stearic alcohol; liquid paraffin; white soft paraffin; polyacrylic acid; sodium hydroxide; disodium EDTA (i.e. ethylenediaminetetraacetic acid disodium salt); methyl and propyl Paraben (i.e. 4-hydroxybenzoic acid methyl and propyl esters); and water.

EXAMPLE II

The white cream of Example I was applied twice daily (morning and either afternoon or evening) to the depigmented areas (vitiligo spots) of several patients suffering from vitiligo. After about 20 minutes following one of said applications, the affected areas were exposed to UVB light for a short period of time to provide a subminimal erythema dose. As the patient's tolerance to UVB light increased, the exposure time was increased from a few seconds to a maximum of about 5 minutes. In all cases, the vitiligo spots were significantly pigmented after a course of treatment of between 3 and 6 months.

The accompanying FIGS. I and II show a typical improvement in the vitiligo patients treated. Both figures show the ear of the same patient. When the patient presented at the clinic, she had several large vitiligo spots including one in the region of the right ear (FIG. I). After three months pseudocatalase/UVB treatment as described above, many of the vitiligo spots had decreased substantially in size including the right ear spot (FIG. II). Pseudocatalase/UVB treatment of this patient continued for a further three months, by which time there was a further substantial reduction in size of the vitiligo spots. The patient was then maintained with pseudocatalase treatment alone.

EXAMPLE III

The procedure of Example 1 was repeated using creams to which calcium chloride had been added to provide 5 millimolar calcium ion content. 18 patients were treated for a mean duration of 4.2 months; 14 of these patients had a partial response and 2 showed a marked, although not complete, pigmentation of vitiliginous skin areas.

EXAMPLE IV

The procedure of Example 1 was repeated using creams to which calcium chloride had been added to provide 10 millimolar calcium ion content. 12 patients were treated for a mean duration of 2.25 months; all had a partial response but none showed signifiacant pigmentation of vitiliginous skin areas.

We claim:

1. A topical composition for treating depigmentation consisting essentially of a pseudocatalase selected from the group consisting of Cu(I) transition metal bicarbonate complex, Fe(II) transition metal bicarbonate complex, and Mn(II) transition metal bicarbonate complex in an amount sufficient to reduce depigmentation in combination with a physiologically acceptable topical vehicle.

2. The composition according to claim 1 wherein the complex is Mn(II)-bicarbonate complex.

3. The composition according to claim 1 wherein the composition contains 5 to 20 millimolar calcium ions.

4. The composition according to claim 3 wherein the complex is Mn(II)-bicarbonate complex.

5. The composition according to claim 2 wherein the Mn(II)-bicarbonate complex is obtained by contacting manganese chloride with excess sodium bicarbonate in aqueous solution.

6. The composition according to claim 5 wherein the composition contains 5 to 20 millimolar calcium ions.

7. A method of pigmenting skin depigmented by a tyrosinase-positive depigmentation disorder which comprises applying to at least the depigmented areas of the skin an effective amount of a pseudocatalase selected from the group consisting of Cu(I) transition metal bicarbonate complex, Fe(II) transition metal bicarbonate complex, and Mn(II) transition metal bicarbonate complex and thereafter exposing the treated skin to UVB light to induce melanin formation in the depigmented areas.

8. The method according to claim 7 wherein the complex is Mn(II)-bicarbonate complex.

9. The method according to claim 7 wherein the composition contains 5 to 20 millimolar calcium ions.

10. The method according to claim 8 wherein the Mn(II)-bicarbonate complex is obtained from contacting manganese chloride with excess sodium bicarbonate in aqueous solution.

11. The method according to claim 10 wherein the composition contains 5 to 20 millimolar calcium ions.

12. A method of treating vitiligo, comprising applying to at least the depigmented areas of the skin a pseudocatalase selected from the group consisting of Cu(I) transition metal bicarbonate complex, Fe (II) transition metal bicarbonate complex, and Mn(II) transition metal bicarbonate complex in an amount sufficient to reduce depigmentation in combination with a physiologically acceptable carrier.

13. The method according to claim 12 wherein the complex is Mn(II)-bicarbonate complex.

14. The method according to claim 12 wherein the composition contains 5 to 20 millimolar calcium ions.

15. The method according to claim 13 wherein the Mn(II)-bicarbonate complex is obtained from contacting manganese chloride with excess sodium bicarbonate in aqueous solution.

16. The method according to claim 15 wherein the composition contains 5 to 20 millimolar calcium ions.

* * * * *